(12) United States Patent
Montgomery et al.

(10) Patent No.: US 11,197,637 B2
(45) Date of Patent: Dec. 14, 2021

(54) CONTROL SYSTEM FOR A VEHICLE SEAT

(71) Applicant: Faurecia Automotive Seating, LLC, Auburn Hills, MI (US)

(72) Inventors: Sean M. Montgomery, Woodside, NY (US); Pioter Drubetskoy, Bronx New York, NY (US)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 157 days.

(21) Appl. No.: 15/626,525

(22) Filed: Jun. 19, 2017

(65) Prior Publication Data

US 2017/0360373 A1 Dec. 21, 2017

Related U.S. Application Data

(60) Provisional application No. 62/352,212, filed on Jun. 20, 2016.

(51) Int. Cl.
*A61B 5/352* (2021.01)
*A61B 5/00* (2006.01)
*A61B 5/024* (2006.01)
*A61B 5/11* (2006.01)
*A61B 5/18* (2006.01)
*B60N 2/00* (2006.01)
*B60N 2/02* (2006.01)

(52) U.S. Cl.
CPC ............ *A61B 5/6893* (2013.01); *A61B 5/024* (2013.01); *A61B 5/02405* (2013.01); *A61B 5/1102* (2013.01); *A61B 5/18* (2013.01); *A61B 5/352* (2021.01); *A61B 5/7221* (2013.01); *B60N 2/002* (2013.01); *B60N 2/0244* (2013.01); *B60N 2002/0268* (2013.01)

(58) Field of Classification Search
CPC ......... A61B 5/046; A61B 5/6893; A61B 5/18; A61B 5/7221; A61B 5/352
See application file for complete search history.

(56) References Cited

U.S. PATENT DOCUMENTS

| | | |
|---|---|---|
| 3,580,245 A | 5/1971 | Dill |
| 4,031,579 A | 6/1977 | Larned |
| 4,655,505 A | 4/1987 | Kashiwamura |
| 4,707,027 A | 11/1987 | Horvath |
| 4,840,425 A | 6/1989 | Noble |

(Continued)

FOREIGN PATENT DOCUMENTS

| | | |
|---|---|---|
| CN | 1572575 | 2/2005 |
| CN | 1956680 A | 5/2007 |

(Continued)

OTHER PUBLICATIONS

Office Action dated Nov. 29, 2017 for U.S. Appl. No. 15/235,882; (pp. 1-7).

(Continued)

*Primary Examiner* — George R Evanisko
(74) *Attorney, Agent, or Firm* — Barnes & Thornburg LLP

(57) ABSTRACT

A system includes a controller coupled to one or more sensors. The controller receives sensor data indicative of biometric data an occupant of a vehicle seat from the sensors. The controller receives the sensor data and analyzes the data to provide biometric data associated with the occupant of the vehicle seat.

8 Claims, 3 Drawing Sheets

(56) References Cited

U.S. PATENT DOCUMENTS

| | | | |
|---|---|---|---|
| 4,928,090 A | 5/1990 | Yoshimi | |
| 5,069,214 A | 12/1991 | Samaras | |
| 5,155,685 A | 10/1992 | Kishi | |
| 5,462,515 A | 10/1995 | Tseng | |
| 6,055,473 A | 4/2000 | Zwolinski | |
| 6,087,942 A | 7/2000 | Sleichter, III | |
| 6,120,468 A | 9/2000 | Tseng | |
| 6,212,719 B1 | 4/2001 | Thomas | |
| 6,273,810 B1 | 8/2001 | Rhodes, Jr. | |
| 6,422,087 B1 | 7/2002 | Potter | |
| 7,206,631 B2 | 4/2007 | Kawachi | |
| 7,239,945 B2 | 7/2007 | Hiemer | |
| 7,322,652 B1 | 1/2008 | Tache | |
| 7,774,052 B2 | 8/2010 | Burton | |
| 7,862,113 B2 | 1/2011 | Knoll | |
| 8,123,290 B1 | 2/2012 | Aiken | |
| 8,181,292 B1 | 5/2012 | Pellettiere | |
| 8,328,279 B2 | 12/2012 | Brncick | |
| 8,430,817 B1 | 4/2013 | Al-Ali | |
| 8,616,654 B2 | 12/2013 | Zenk | |
| 8,672,411 B2 | 3/2014 | Gomes | |
| 8,725,311 B1 | 5/2014 | Breed | |
| 8,757,726 B2 | 6/2014 | Oota | |
| 8,919,874 B2 | 12/2014 | Ota | |
| 9,135,803 B1 | 9/2015 | Fields | |
| 9,440,657 B1 | 9/2016 | Fields | |
| 9,475,389 B1 | 10/2016 | Fung | |
| 9,505,402 B2 | 11/2016 | Fung | |
| 9,717,345 B1 | 8/2017 | Caruso | |
| 9,771,003 B2 | 9/2017 | Kolich | |
| 9,848,814 B2 | 12/2017 | Benson | |
| 10,179,525 B2 | 1/2019 | Arata | |
| 10,235,859 B1 | 3/2019 | Hiles | |
| 10,258,535 B2 | 4/2019 | Lem | |
| 10,471,864 B1 | 11/2019 | Tait | |
| 2002/0091473 A1 | 7/2002 | Gardner | |
| 2004/0243368 A1 | 12/2004 | Hiemer | |
| 2005/0027416 A1 | 2/2005 | Basir | |
| 2005/0124864 A1 | 6/2005 | Mack | |
| 2005/0248184 A1 | 11/2005 | Piffaretti | |
| 2006/0025698 A1* | 2/2006 | Nakagawa | A61B 5/0408 600/513 |
| 2006/0068693 A1 | 3/2006 | Kono | |
| 2006/0175877 A1 | 8/2006 | Alionte | |
| 2007/0029862 A1 | 2/2007 | Bargheer | |
| 2007/0251749 A1 | 11/2007 | Breed | |
| 2008/0296946 A1 | 12/2008 | Reynolds | |
| 2009/0030576 A1 | 1/2009 | Periot | |
| 2009/0164241 A1 | 6/2009 | Racioppo | |
| 2010/0185068 A1 | 7/2010 | Park | |
| 2010/0229181 A1 | 9/2010 | Ahuja | |
| 2011/0015468 A1 | 1/2011 | Aarts | |
| 2011/0066292 A1 | 3/2011 | Moriya | |
| 2011/0133755 A1 | 6/2011 | Griffin | |
| 2011/0156453 A1 | 6/2011 | Matsushima | |
| 2011/0186560 A1 | 8/2011 | Kennedy | |
| 2011/0304465 A1 | 12/2011 | Boult | |
| 2012/0078123 A1* | 3/2012 | Futatsuyama | A61B 5/0402 600/485 |
| 2012/0212353 A1 | 8/2012 | Fung | |
| 2013/0070043 A1 | 3/2013 | Geva | |
| 2014/0031703 A1 | 1/2014 | Rayner | |
| 2014/0039330 A1* | 2/2014 | Seo | A61B 5/02 600/509 |
| 2014/0228649 A1 | 8/2014 | Rayner | |
| 2014/0240132 A1 | 8/2014 | Bychkov | |
| 2014/0276112 A1 | 9/2014 | Fung | |
| 2015/0008710 A1 | 1/2015 | Young | |
| 2015/0051526 A1 | 2/2015 | Wang | |
| 2015/0151658 A1 | 6/2015 | Burris | |
| 2015/0231991 A1 | 8/2015 | Yetukuri | |
| 2015/0239321 A1 | 8/2015 | Müller | |
| 2015/0313475 A1 | 11/2015 | Benson | |
| 2016/0001781 A1 | 1/2016 | Fung | |
| 2016/0019813 A1 | 1/2016 | Mullen | |
| 2016/0029940 A1 | 2/2016 | Iizuka | |
| 2016/0086500 A1 | 3/2016 | Kaleal, III | |
| 2016/0339801 A1 | 11/2016 | Pereny | |
| 2016/0339802 A1 | 11/2016 | Hanlon | |
| 2017/0136842 A1 | 5/2017 | Anderson | |
| 2017/0136922 A1 | 5/2017 | Von Ballmoos | |
| 2017/0158202 A1 | 6/2017 | Yang | |
| 2017/0282930 A1 | 10/2017 | Kochhar | |
| 2017/0285641 A1 | 10/2017 | Goldman-Shenhar | |
| 2017/0312534 A1* | 11/2017 | Cao | A61N 1/3987 |
| 2017/0326013 A1 | 11/2017 | Hyde | |
| 2017/0340214 A1 | 11/2017 | Benson | |
| 2018/0037236 A1 | 2/2018 | Yamaguchi | |
| 2018/0178808 A1 | 6/2018 | Zhao | |
| 2018/0229674 A1 | 8/2018 | Heinrich | |

FOREIGN PATENT DOCUMENTS

| | | | |
|---|---|---|---|
| CN | 103565429 A | 2/2014 | |
| CN | 104837403 A | 8/2015 | |
| CN | 0104875744 | 9/2015 | |
| DE | 102005038289 | 3/2007 | |
| DE | 102007053119 | 5/2009 | |
| DE | 102009021532 | 11/2010 | |
| EP | 1447070 A | 8/2004 | |
| JP | 2010264092 | 11/2010 | |
| KR | 1020010061858 | 7/2001 | |
| KR | 1020140027641 | 3/2014 | |
| KR | 0101642697 | 8/2016 | |
| WO | 2013109154 | 7/2013 | |
| WO | 2013109154 A1 | 7/2013 | |
| WO | 02014147828 | 9/2014 | |
| WO | 2014147828 | 9/2014 | |
| WO | WO-2015/127193 * | 8/2015 | A61M 21/02 |
| WO | 2015200224 | 12/2015 | |
| WO | 2016070981 | 5/2016 | |

OTHER PUBLICATIONS

European Examination Report for European App. No. 15 707 235.6 dated Feb. 6, 2018, 7 pages.

Chinese Office Action for Chinese Pat. App. No. 201580011844.9 dated Mar. 14, 2019, 12 pages, (brief summary included in English).

Chinese Rejection Decision for Chinese App. No. 201380064313.2 dated May 17, 2018, 13 pages.

Chinese Office Action for Chinese Pat App. No. 201580011844.9 dated Aug. 28, 2018, 19 pages, (brief summary included in English).

Chinese Office Action for Chinese App. No 201380064313.2 dated Apr. 12, 2017, 21 pages.

PCT International Search Report and Written Opinion completed by the ISA/US dated Apr. 22, 2014 and issued in connection with PCT/US2013/071620.

PCT Search Report and Written Opinion completed by the ISA/EP dated May 21, 2015 and issued in connection with PCT/US2015/016803, 13 pages.

Chinese Office Action for Chinese App. No. 201380064313.2 dated Sep. 28, 2017, 19 pages.

Office Action dated May 1, 2019 for U.S. Appl. No. 15/692,396, (pp. 1-27).

Chinese Office Action for Chinese Pat. App. No. 201580011844.9 dated Jul. 12, 2019, 13 pages, (brief summary included in English).

Chinese Office Action for Chinese Pat. App. No. 201580011844.9 dated Nov. 19, 2019, 13 pages, (brief summary included in English).

Office Action dated Mar. 4, 2020 fo U.S. Appl. No. 15/678,710, (pp. 1-14).

Office Action dated Apr. 30, 2020 for U.S. Appl. No. 15/873,034, (pp. 1-24).

European Examination Report for European App. No. 15 707 235.6 dated Apr. 15, 2020, 5 pages.

Office Action dated Apr. 30, 2020 for U.S. Appl. No. 15/863,129, (pp. 1-23).

Office Action dated May 8, 2020 for U.S. Appl. No. 15/613,578, (pp. 1-23).

N. Mizuno and K. Washino, "A model based filtering technique for driver's heart rate monitoring using seat-embedded vibration sen-

(56) References Cited

OTHER PUBLICATIONS sors," 2014 6th International Symposium on Communications, Control and Signal Processing (ISCCSP), Athens, 2014, pp. 137-140, doi: 10.1109/ISCCSP.2014.6877834. (Year: 2014).

Second Chinese Office Action for Chinese App. No. 201710799929.9 dated Jul. 1, 2020, 6 pages.

Fifth Chinese Office Action for Chinese Pat. App. No. 201580011844.9 dated Mar. 13, 2020, 13 pages, (brief summary included in English).

Choi et al., "Noninvaisive cuffless blood pressure estimation usingpulse transit time and Hilbert-Huang transform," Computers and Electridal Engineering Journal, 39, 103-111 (Nov. 8, 2012), 9 pages.

Wong et al., "The Effects of Exercises on teh Relationship between Pulse Transit Time and Arterial Blood Pressure," Proceedings of the 2005 IEEE Enginering in Medicine and Biology 27th Annual Conference, Shanghai, China, Sep. 1-4, 2005, 3 pages.

Office Action dated Feb. 1, 2021 for U.S. Appl. No. 15/863,129, (pp. 1-16).

Office Action dated Feb. 1, 2021 for U.S. Appl. No. 15/873,034, (pp. 1-19).

Office Action dated Sep. 3, 2020 for U.S. Appl. No. 15/863,129, (pp. 1-15).

Office Action dated Sep. 3, 2020 for U.S. Appl. No. 15/873,034, (pp. 1-17).

Office Action dated Sep. 3, 2019 for U.S. Appl. No. 15/613,578, (pp. 1-20).

Chinese Office Action for Chinese App. No 201710799929.9 dated Sep. 27, 2019, 14 pages.

Office Action dated Oct. 29, 2019 for U.S. Appl. No. 15/692,396, (pp. 1-37).

\* cited by examiner

CONTROL SYSTEM FOR A VEHICLE SEAT

PRIORITY CLAIM

This application claims priority under 35 U.S.C. § 119(e) to U.S. Provisional Application Ser. No. 62/352,212, filed Jun. 20, 2016, which is expressly incorporated by reference herein.

BACKGROUND

The present disclosure relates to an electronic system, and particularly to an electronic system for a vehicle seat. More particularly the present disclosure relates to an electronic system for a vehicle seat including one or more sensors.

SUMMARY

According to the present disclosure, an occupant support includes a vehicle seat and a controller coupled to the vehicle seat to control the vehicle seat. The controller includes a sensor module configured to receive sensor data and a processing module configured to process the sensor data.

In illustrative embodiments, the controller is configured to make biometric measurements of a vehicle-seat occupant. The sensor module is configured to receive sensor data indicative of a heartbeat of an occupant of a vehicle seat from one or more sensors of a vehicle. The processing module is configured to identify peaks in the sensor data based on a dynamic peak detection threshold, to score the identified peaks with a reliability score, and remove unreliable peaks.

In illustrative embodiments, the controller further includes a biometrics module. The biometrics module is configured to determine biometric data associated with the occupant based on reliably identified peaks.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figure 1:
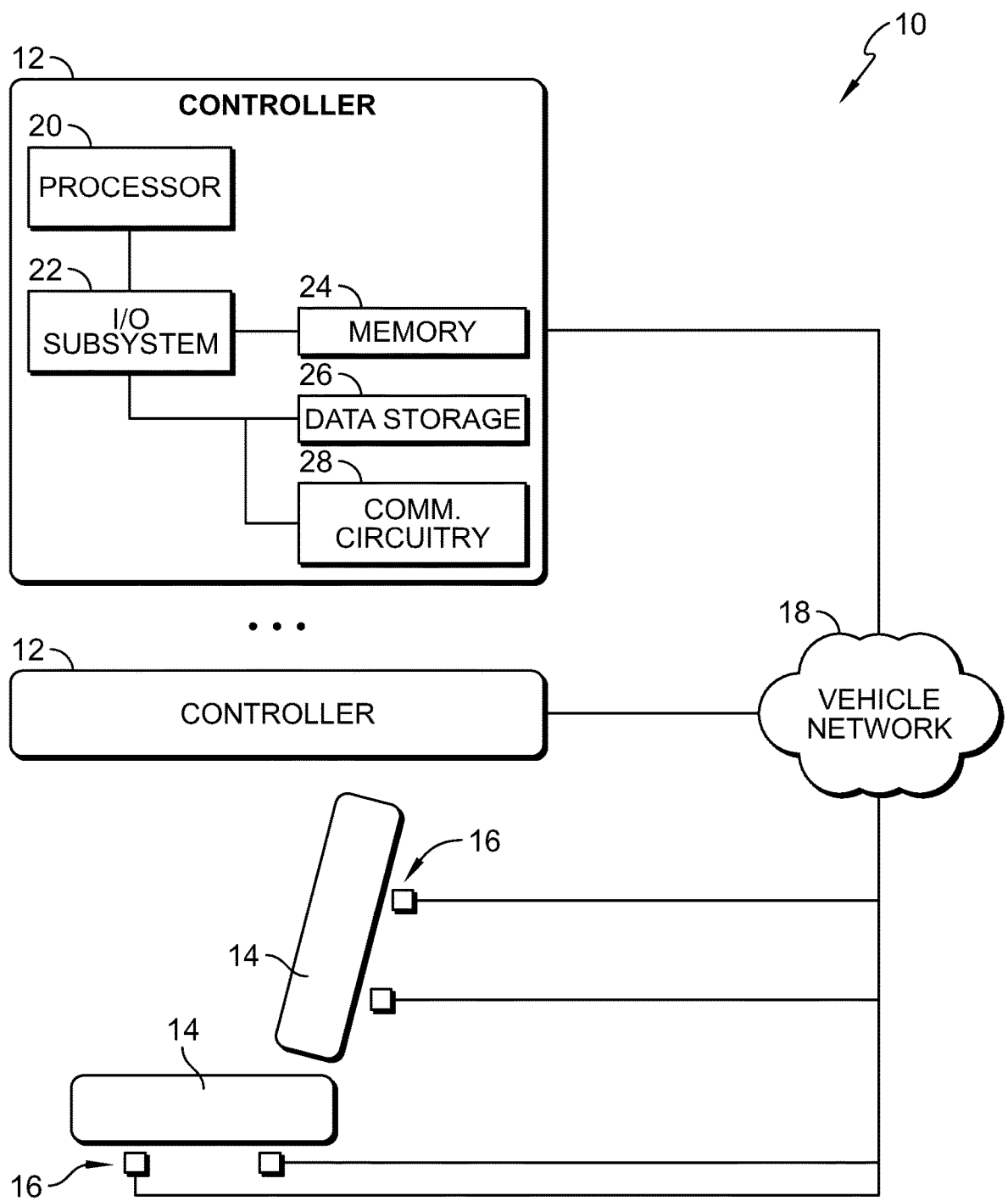
FIG. 1 is a diagrammatic view of a system in accordance with the present disclosure showing a vehicle seat, a controller, and multiple sensors coupled to the controller.

A system 10 in accordance with the present disclosure is shown in FIG. 1. The system 10 may be included in a vehicle such as a car or truck (not shown). The illustrative system 10 includes multiple controllers 12, a vehicle seat 14, multiple sensors 16, and a vehicle network 18. As described further below, in use, a controller 12 may receive sensor data from the sensors 16 and determine biometric data relating to an occupant of the vehicle seat 14 based on the sensor data.

The illustrative vehicle seat 14 may be embodied as an adjustable or otherwise movable vehicle seat and may include multiple parts, including a seat bottom, seat back, and/or head restraint. The vehicle seat 14 may include one or more controllers, actuators, and/or other components to provide one or more therapies. Therapies may include active surface movement including massage, lumbar and bolster, postural adjustment, and other moveable surfaces that enable and/or encourage postural movement. Climate therapies may include heat, cool, venting, scent, air quality, lighting (red/blue), and music and may also be used.

As shown, the vehicle seat 14 is coupled to multiple sensors 16. Each of the sensors 16 may be embodied as any electronic device capable of measuring vibrations generated by biological processes of an occupant of the vehicle seat (e.g., vibrations caused by the occupant's heartbeat, respiration, or other processes). In the illustrative embodiment, the sensors 16 are embodied as blood oxygenation, electrocardiogram (ECG), ballistocardiogram (BCG) sensors, combinations thereof, or any other suitable alternative. The sensors 16 may include piezoelectric cables, accelerometers (piezoelectric), microphones, impedance field or other vibration sensors. The sensors 16 may be included in, incorporated in, or otherwise attached to the vehicle seat 14. Thus, in some embodiments, the sensors 16 may be covered with vehicle seat trim and accordingly spaced apart from the occupant of the vehicle seat 14. Additionally, although illustrated as including four sensors 16, other embodiments of the system 10 may include a different number and/or arrangement of sensors 16.

The system 10 further includes one or more controllers 12, which each may be embodied as an electronic control unit or other controller configured to perform the functions described herein. In particular, and as described further below, a controller 12 (e.g., a controller 12 coupled to the vehicle seat 14) may be configured receive sensor data from the sensors 16 and determine biometric data relating to the occupant of the vehicle seat 14 based on the sensor data. Thus, the system 10 may measure occupant biometrics even in a noisy environment such as the interior of a vehicle when driving. Additionally, the system 10 may measure occupant biometrics with the sensors 16 spaced apart from the occupant's body (e.g., to allow for seat trim and clothing), without requiring the sensors 16 to be attached to the occupant. By measuring the occupant biometrics, the system 10 may provide biofeedback to the occupant, trigger or suggest appropriate therapies, or perform other applications.

Figure 2:
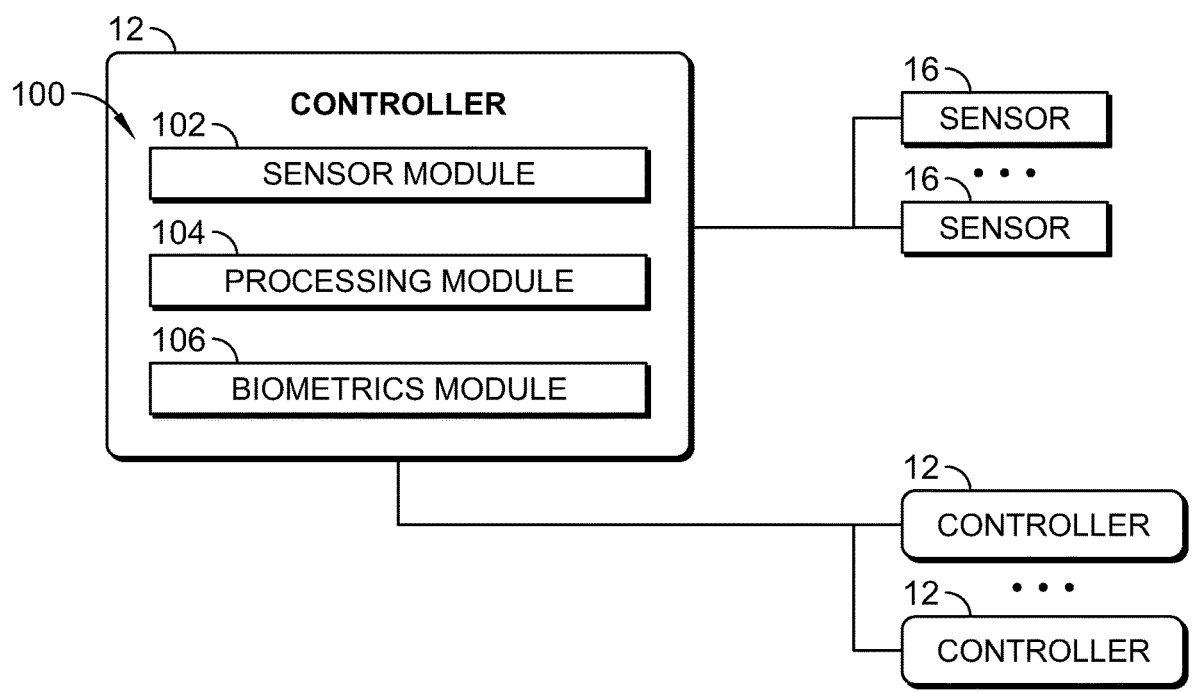
FIG. 2 is a diagrammatic view of at least one embodiment of an environment that may be established by a controller of FIG. 1.

Referring now to FIG. 2, in the illustrative embodiment, a controller 12 establishes an environment 100 during operation. The illustrative environment 100 includes a sensor module 102, a processing module 104, and a biometrics module 106. The various modules of the environment 100 may be embodied as hardware, firmware, software, or a combination thereof. For example the various modules, logic, and other components of the environment 100 may form a portion of, or otherwise be established by, the processor 20 or other hardware components of the controller 12. As such, in some embodiments, any one or more of the modules of the environment 100 may be embodied as a circuit or collection of electrical devices (e.g., sensor circuitry, processing circuitry, biometrics circuitry, etc.).

The sensor module 102 is configured to receive sensor data indicative of a heart rate of an occupant of the vehicle seat 14 from one or more sensors 16 of the vehicle. As described above, the sensors 16 may include, for example, ECG or BCG sensors.

The processing module 104 is configured to determine a peak detection function for the occupant heartbeat sensor data. The peak detection function identifies the peaks in the PQRST complex in the sensor data. For example, the peak function may include a threshold dynamically set based on the height of the last detected R peak and a time-dependent decay. In some embodiments, the peak detection function may be set dynamically based on determined interbeat intervals (IBI's) detected in the sensor data. IBI's are the time elapsed between consecutive peaks in the heartbeat signal. The processing module 104 is further configured to apply the peak detection function to the sensor data to generate peak sensor data.

The processing module 104 further includes an algorithm to determine individual-specific reliability of the peak sensor data. The reliability assessment provides each detected peak with a score so that highly reliable data may be emphasized through weighting the effect of poor and errant data may be minimized or eliminated in biometric analyses. As a result of this weighting, variations are not muted as is typical in smoothing through averaging or filtering. In some embodiments, the system may include two different sensors 16, such as ECG and BCG, and one or more controllers 12 may be used to determine which of the two sensors is providing reliable measurements at that point in time for biometric analyses.

The biometrics module 106 is configured to determine biometric data associated with the occupant of the vehicle seat 14 based on the verified reliable peak sensor data. For example, the biometrics module 106 may be configured to determine a heart rate, a heart rate variability, and/or a stress metric.

Figure 3:
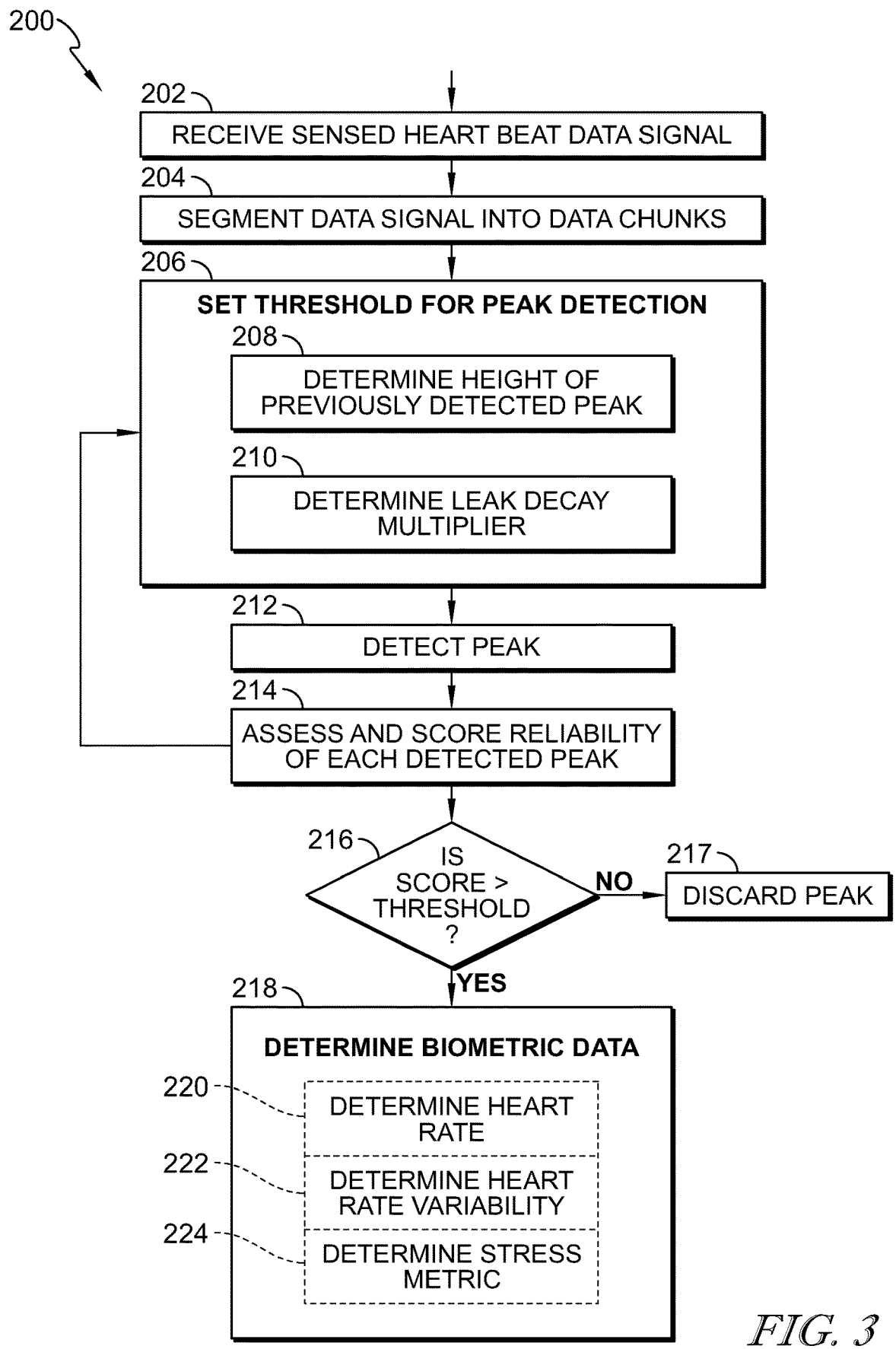
FIG. 3 is a flow diagram illustrating at least one embodiment of a method for determining reliably occupant biometric data that may be executed by the controller of FIGS. 1 and 2.

Referring now to FIG. 3, in use, the controller 12 may execute a method 200 for determining biometric data of an occupant of the vehicle seat 14. In some embodiments, the operations of the method 200 may be performed by one or more modules of the environment 100 of the controller 12 as shown in FIG. 2. The method 200 begins in block 202, in which the controller 12 receives heartbeat sensor data from one or more sensors 16. The heartbeat sensor data is indicative of heart rate caused by an occupant of the vehicle seat 14.

In block 204, the controller 12 segments the collected heartbeat signal data into chunks. For example, the collected data may be broken down, or segmented, into 100 ms to 1000 ms chunks of the collected signal for processing. At 206, controller sets the threshold for peak identification in the data chunks by determining the height of the last identified peak 208 and the leak decay multiplier 210. In some embodiments the leak decay multiplier may be a constant value if the heart beat is regular and steady. For example, the leak decay multiplier may be set to 0.5/second, so that after one second of no detected peaks, the amplitude threshold for peak detection is half the last peak amplitude. In one example, the leak decay multiplier is dynamically set by determining the IBI's (inter-beat intervals). For example, the leak decay multiplier may be dynamically adjusted so that the threshold decays faster during periods of short IBI's and slower during periods of long IBI's. Based on the determined threshold, the controller detects a peak 212 in the segment and the threshold setting process 206 and peak detection 212 are repeated until all peaks are detected in each data chunk.

In some embodiments the data chunks may be segmented at 204 into sequential, non-overlapping chunks of heart rate data. In some embodiments, the data chunks may be segmented at 204 into overlapping chunks of data. This overlapping segmentation provides a more continuous leak decay by avoiding edge effects within a given chunk of data. In this circumstance, overlapping, or repetitively detected peaks would be filtered out based on timestamps for the data to avoid duplication in peak detection.

Once all peaks have been detected in a given data chunk, the reliability of each detected peak may be assessed and assigned a score 214. This assessment may use several convergent measures to assess reliability of the detected peak given the sometimes highly variable changes in heart rate. The assessment may employ logic to determine the similarity of the current IBI with an average previously discovered IBI's, and the overall distribution quality, as peaky distributions are more trustworthy than multi-modal distributions. The average previously discovered IBI's may be stored in the controller for vehicle occupants.

The assessment logic employed to assign a score 214 includes discarding any IBI that is too short. For an adult this may be any IBI that is less than 290 ms. For a child this may be adjusted using the calculation HRmax=220−age. For example a HRmax of 206 BPM has a minimum IBI of 190 ms. IBI's not meeting the minimum time may be considered to not meet the score threshold 216 and are discarded 217.

Next, the reliability of each detected peak meeting the minimum IBI time may be determined by applying the following logic:

1) Calculate the median IBI from the IBI distribution.
2) Calculate by how much the current IBI deviated from the median previously discovered IBI (denote this delta).
3) Calculate the Median Absolute Deviation (MAD) of the IBI distribution. It was used 1.5*MAD as a proxy for standard deviation of the IBI distribution.
4) Calculate the delta reliability, r(delta), as a sigmoid with the argument delta/(1.5*MAD). The lower the delta (normalized by the standard deviation), the higher the reliability and vice versa, with the reliability falling off sharply after a certain threshold (depending on the parameters of the sigmoid function).
5) Calculate the ratio of MAD of IBI distribution to MAD of a uniform distribution on the range of +/−80*log(n) around the median of IBI distribution (where n is the size of the IBI buffer). This measure, denoted as "H," may be used to assess the general non-uniformity of the IBI distribution, with the idea that the more uniform and wider the distribution, the less it is trustworthy.
6) The reliability of the distribution, r(distribution) is then determined as linearly decreasing with this measure: 1−min (H,1).
7) The total reliability score, or reliability, of the peak/IBI is calculated as a geometric average of the delta reliability and the distribution reliability, namely, sqrt(r(delta)*r(distribution).

In some embodiments, peak amplitude distribution may be incorporated into the total reliability calculation. In some embodiments measures of signal to noise ratio may be used to assess the quality of the heartbeat signal and logic may be applied to each sensor at the point of receipt of the signal. In some embodiments additional filtering such as a Kalman filter may be applied to the IBI.

In some embodiments, peak amplitude distribution may be incorporated into the total reliability calculation. In some embodiments measures of signal to noise ratio may be used to assess the quality of the heartbeat signal and logic may be applied to each sensor at the point of receipt of the signal. In some embodiments additional filtering such as a Kalman filter may be applied to the IBI.

In 214, the controller determines whether the total reliability score is above a predetermined threshold. In some embodiments, this threshold is 50%. If the score is not above that threshold, the peak data is discarded 216. If the score is above the threshold, the peak data may be used to calculate biometric data 218.

In some embodiments, the heart rate is calculated with the IBI's 220. In some embodiments, a signal of heart rates with their corresponding timestamps and reliabilities may be used to calculate the average heart rate for an occupant. In some embodiments this average heart rate is determined as a weighted average heart rate, causing older heart rate data to be less relevant to the current average heart rate calculation.

In order to determine the weighted average heart rate, a decay may be determined for each heart rate as am exponential; of the time difference between the time of the heart rate and the current time minus the time of the calculation, scaled by an appropriate constant:

$$decay_i = \exp\left(-\frac{timeNow - time_i}{scale}\right)$$

The average heart rate may then be weighted using the following calculation with weights given by decay*reliability.

$$\frac{\sum_i HR_t \times reliablity_i \times decay_i}{\sum_i reliability_i \times decay_i}$$

Average reliability of the average heart rate may be calculated as the weighted average of the reliabilities weighted by decay along with a multiplier of the last calculated decay. Average reliability may be calculated as follows:

$$\frac{\sum_i reliablity_i \times decay_i}{decay_i} \times decay_N$$

In this manner, the control gives decreased reliability to a heart rate signal as the signal becomes older or stale. Average heart rate above a certain reliability score can be identified as reliable. In some embodiments the decay may only be applied to average IBI after a certain period of time has passed. In some embodiments an additional parameter may be introduced to account for the non-uniformity of a heart rate signal distribution over time.

In some embodiments heart rate variability (HRV) may be determined 222. This may be done by buffering the IBI's and associated timestamps of the IBI's over a long interval. In some embodiments, this interval may be several minutes. The IBI buffer along with the timestamps may be analyzed using, for example, a Lomb-Scargle Periodogram or any other FFT (fast Fournier transform) analysis capable of estimating spectral power of unevenly sampled signals. This generates a HRV spectrum of the variability.

In some embodiments the reliability score threshold for allowing peaks into the biometric data determination may be lowered, thereby permitting more variability to be introduced into this determination. In some embodiments, the buffering includes the previous 64 IBI's. In some embodiments the length of buffer may be a particular duration of time, such as minutes, instead of a number of IBI's.

In some embodiments, the IBI buffer may be spline resampled at a fixed sampling rate to determine the contribution of the sympathetic nervous system to the HRV. The contribution of the sympathetic nervous system can be calculated as the ratio between the low frequency changes (LF; 0.04-0.15 Hz) and high frequency changes (HF; 0.15-0.4 Hz) described by the formula LF/(LF+HF).

In some embodiments, the biometric data calculated may include a stress metric 224. A smoothing operation the ratio described above as the contribution of the sympathetic nervous system may be performed in order to determine the stress metric. For example, the ratio may be squared so that the resultant value directly correlates to emotional stress, or sympathetic nervous system contribution. For example 100% would be the highest stress contribution and 0% would be the lowest stress contribution.

Each controller 12 may be embodied as any device capable of performing the functions described herein. For example, each controller 12 may be embodied as an electronic control unit, embedded controller, control circuit, microcontroller, computing device, on-board computer, and/or any other any other computing device capable of performing the functions described herein. As shown in FIG. 1, an illustrative controller 12 includes a processor 20, an I/O subsystem 22, a memory 24, a data storage device 26, and communication circuitry 28. The controller 12 may include other or additional components, such as various input/output devices or any other suitable components. Additionally, in some embodiments, one or more of the illustrative components may be incorporated in, or otherwise form a portion of, another component. For example, the memory 24, or portions thereof, may be incorporated in the processor 20 in some embodiments.

The processor 20 may be embodied as any type of processor capable of performing the functions described herein. For example, the processor 20 may be embodied as a microcontroller, digital signal processor, single or multi-core processor(s), or other processor or processing/controlling circuit. Similarly, the memory 24 may be embodied as any type of volatile or non-volatile memory or data storage capable of performing the functions described herein. In operation, the memory 24 may store various data and software used during operation of the processor 20 such as operating systems, applications, programs, libraries, and drivers. The memory 24 is coupled to the processor 20 via the I/O subsystem 22, which may be embodied as circuitry and/or components to facilitate input/output operations with the processor 20, the memory 24, and other components of the controller 12. For example, the I/O subsystem 22 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 22 may form a portion of a system-on-a-chip (SoC) and be incorporated, along with the processor 20, the memory 24, and other components of the controller 12, on a single integrated circuit chip.

The data storage device 26 may be embodied as any type of device or devices configured for short-term or long-term storage of data such as, for example, memory devices and circuits, memory cards, hard disk drives, solid-state drives, read-only memory, or other data storage devices. The communication circuitry 28 of the controller 12 may be embodied as any communication circuit, device, or collection thereof, capable of enabling communications between the controller 12 and other devices of the vehicle seat 14 and/or the vehicle. The communication circuitry 28 may be configured to use any one or more communication technology (e.g., wireless or wired communications) and associated protocols (e.g., Ethernet, controller area network (CAN), local interconnect network (LIN), Bluetooth®, Wi-Fi®, etc.) to effect such communication. In some embodiments, the communication circuitry 28 may include one or more general-purpose I/O pins, analog interfaces, solid state motor control electronics, and/or other circuitry that may be used to interface with or otherwise control features of the vehicle seat 14 (e.g., seat motion, therapy, or other features).

As further shown in FIG. 1, the controllers 12 and the sensors 16 may be configured to transmit and/or receive data with each other and/or other devices over the vehicle network 18. The vehicle network 18 may be embodied as any bus, network, or other communication facility used to communicate between devices in the vehicle. For example, the vehicle network 18 may be embodied as a wired or wireless local area network (LAN), controller area network (CAN), and/or local interconnect network (LIN). Thus, the vehicle controllers 12 may include one or more additional electronic control units, embedded controllers, engine computers, or other computing devices used to control various vehicle functions. In particular, the controller 12 may be configured to communicate with one or more additional vehicle controllers 12 via the vehicle network 18 to determine the state of the vehicle, for example to determine whether the ignition is on, to determine engine speed or engine load, to determine vehicle speed, or to determine other vehicle state. Additionally or alternatively, although shown as communicating directly with the vehicle network 18, in some embodiments the sensors 16 may be coupled directly to one or more controllers 12 (e.g., a seat controller 12) without using the vehicle network 18.

The invention claimed is:

1. A controller for biometric measurement of a vehicle occupant, the controller comprising
    a plurality of sensors including a piezoelectric sensor and a second sensor configured to detect sensor data indicative of a heartbeat signal for an occupant of a vehicle seat, wherein the sensor data comprises a last detected peak, a height of the last detected peak, a plurality of heartbeat peaks including reliably identified peaks and unreliably identified peaks, and a detected inter-beat interval (IBI),
    processing circuitry configured to identify the last detected peak, the height of the last detected peak, the plurality of reliably identified peaks, the plurality of unreliably identified peaks, and the detected IBI in the sensor data,
    wherein the processing circuitry determines a leak decay multiplier and a dynamic peak detection threshold, wherein the dynamic peak detection threshold is continuously updated by the processing circuitry based on the leak decay multiplier;
    wherein the processing circuitry determines a reliability score for each of the heartbeat peaks based on the dynamic peak detection threshold, wherein the reliability score is used by the processing circuitry to provide the reliably identified peaks and the unreliably identified peaks and remove the unreliably identified peaks, and
    biometrics circuitry configured to determine biometric data associated with the occupant based on the reliably identified peaks,
    wherein the processing circuitry dynamically adjusts the leak decay multiplier based on the detected IBI in the heartbeat signal so that the dynamic peak detection threshold decays faster during periods of short IBI's and slower during periods of long MI's, and
    wherein the processing circuitry compares the sensor data of the plurality of sensors for reliability, and the reliably identified peaks of a current more reliable sensor of the plurality of sensors are provided to the biometrics circuitry.

2. The controller of claim 1, further comprising scoring logic, wherein the processing circuitry uses the scoring logic to score the reliability of the reliably identified peaks and the unreliably identified peaks.

3. The controller of claim 1, wherein the processing circuitry determines an IBI distribution of the received sensor data and a distribution of previously identified peaks, and wherein the reliability score for each peak is determined based on a comparison, by the processing circuitry, of the IBI distribution of the received sensor data with the distribution of the previously identified peaks.

4. The controller of claim 1, wherein the biometrics circuitry calculates a heart rate variability of the occupant based on the reliably identified peaks.

5. The controller of claim 4, wherein the biometrics circuitry determines a contribution of the sympathetic nervous system to the calculated heart rate variability.

6. The controller of claim 1, wherein the sensor data comprises the heartbeat signal of the occupant of the vehicle and the heartbeat peaks in the sensor data are indicative of R-peaks in a PQRST Complex.

7. The controller of claim 1, wherein the processing circuitry automatically updates the dynamic peak detection threshold according to selected time periods.

8. The controller of claim 1, wherein processing circuitry segments the sensor data into overlapping data chunks and filters repetitively detected peaks to remove duplicates.

* * * * *